(12) United States Patent
Ueda et al.

(10) Patent No.: US 8,574,568 B2
(45) Date of Patent: Nov. 5, 2013

(54) REDUCED COENZYME Q10-CONTAINING COMPOSITION COMPRISING A SURFACTANT WHICH IS STABLE AGAINST OXIDATION AND METHOD FOR STABILIZATION BY MIXING WITH SURFACTANT(S)

(75) Inventors: Takahiro Ueda, Kobe (JP); Shiro Kitamura, Akashi (JP)

(73) Assignee: Kaneka Corporation, Osaka (JP)

( * ) Notice: Subject to any disclaimer, the term of this patent is extended or adjusted under 35 U.S.C. 154(b) by 253 days.

(21) Appl. No.: 12/092,925

(22) PCT Filed: Nov. 7, 2006

(86) PCT No.: PCT/JP2006/322139
§ 371 (c)(1),
(2), (4) Date: Oct. 31, 2008

(87) PCT Pub. No.: WO2007/052802
PCT Pub. Date: May 10, 2007

(65) Prior Publication Data
US 2009/0181002 A1    Jul. 16, 2009

(30) Foreign Application Priority Data

Nov. 7, 2005 (JP) ................................. 2005-321798

(51) Int. Cl.
*A61K 31/15* (2006.01)
*A61K 47/14* (2006.01)

(52) U.S. Cl.
USPC ............................ 424/94.1; 549/409; 528/272

(58) Field of Classification Search
USPC ............................ 424/94.1; 549/409; 528/272
See application file for complete search history.

(56) References Cited

U.S. PATENT DOCUMENTS

| | | | |
|---|---|---|---|
| 4,827,062 A | 5/1989 | Saeki et al. | |
| 5,089,404 A | 2/1992 | Matsumoto et al. | |
| 5,401,867 A | 3/1995 | Sitzmann et al. | |
| 6,200,550 B1 * | 3/2001 | Masterson et al. | 424/49 |
| 6,562,869 B1 * | 5/2003 | Hamilton et al. | 514/557 |
| 6,740,338 B1 * | 5/2004 | Chopra | 424/456 |
| 7,767,241 B2 | 8/2010 | Kuwabara et al. | |
| 2004/0126367 A1 | 7/2004 | Fujii et al. | |
| 2009/0264667 A1 | 10/2009 | Kellens et al. | |

FOREIGN PATENT DOCUMENTS

| | | |
|---|---|---|
| EP | 0 979 654 A1 | 2/2000 |
| JP | 61-221131 A | 10/1986 |
| JP | 62-223119 A | 10/1987 |
| JP | 62-298526 A | 12/1987 |
| JP | 2003-26625 A | 1/2003 |
| JP | 2005-47851 A | 2/2005 |
| WO | 99/44617 A1 | 9/1999 |

OTHER PUBLICATIONS

Kreulen, H.P., "Fractionation and winterization of edible fats and oils", J. Am. Oil Chem. Soc., 1976, vol. 53, pp. 393-396.
Cousins, E.R., "Hydrogenation of fats and oils. Isomerization during hydrogenation", J. Am. Oil Chem. Soc., vol. 40, pp. 206-210.
Rheodol TW-O120V, Kao Chemicals, [retrieved on Jul. 18, 2011]. Retrieved from the Internet:<URL:http://chemical.kao.com/global/products/B0008750_glen.html>.
Kaohomotex PS-200V, Kao Chemicals, [retrieved on Jul. 18, 2011]. Retrieved from the Internet:<http://chemical.kao.com/global/products/B0008037_glen.html>.
Propylene glycol esters of fatty acids, Compendium of food additive specifications. Addendum 5., FAO Corporate Document Repository, [retrieved on Jul. 18, 2011]. Retrieved from the Internet:<URL:http://www.fao.org/docrep/w6355e/w6355e0v.htm>.
Wikipedia, the free encyclopedia, entry on Polysorbate 80, [retrieved on Oct. 31, 2011]. Retrieved from the Internet:<URL:http://en.wikipedia.org/wiki/Polysorbate_80>.
Abstract of an article by T. Abeshima, "Fractionation of edible oils and fats," Nikon yukagaku kaishi, vol. 47, pp. 553-561, 1998, [retrieved on May 14, 2012]. Retrieved from the Internet:<URL:http://cat.inist.fr/?aModele=afficheN&cpsidt=2374831>.
Abstract of an article by W. Hamm, "Trends in edible oil fractionation," Trends in Food Science & Technology, vol. 6, pp. 121-126, 1995, [retrieved on May 14, 2012], Retrieved from the Internet:<URL:http://www.sciencedirect.com/science/article/pii/S0924224400889955>.
W. Hamm, Fractionation Technology, [retrieved on May 14, 2012]. Retrieved from the Internet:<URL:http://www.britanniafood.com/download/?mode=dynamic&id=3>.
G. Calliauw, "Edible Oil Processing, Dry Fractionation," The AOCS Lipid Library, [retrieved on May 14, 2012]. Retrieved from the Internet:<URL:http://lipidlibrary.aocs.org/processing/dryfract/index.htm>.
"Dry Fractionation of Lipids," [retrieved on May 14, 2012], Retrieved from the Internet:<URL:http://www.cyberlipid.org/fraction/frac0011.htm>.

* cited by examiner

*Primary Examiner* — Rosanne Kosson
(74) *Attorney, Agent, or Firm* — Sughrue Mion, PLLC

(57) ABSTRACT

The present invention provides a method for stabilization of reduced coenzyme $Q_{10}$ characterized by concurrently containing a propylene glycol fatty acid ester in a composition containing reduced coenzyme $Q_{10}$, and a composition containing reduced coenzyme $Q_{10}$ and a propylene glycol fatty acid ester as essential constituting ingredients. According to the present invention, reduced coenzyme $Q_{10}$, which is useful as a food, food with nutrient function claims, food for specified health use, nutritional supplement, nutritional product, animal drug, drink, feed, cosmetic, pharmaceutical product, therapeutic drug, prophylactic drug and the like can be stabilized especially without being made into a complicated composition.

29 Claims, No Drawings

REDUCED COENZYME Q10-CONTAINING COMPOSITION COMPRISING A SURFACTANT WHICH IS STABLE AGAINST OXIDATION AND METHOD FOR STABILIZATION BY MIXING WITH SURFACTANT(S)

CROSS REFERENCE TO RELATED APPLICATION

This application is a National Stage of International Application No. PCT/JP2006/322139 filed on Nov. 7, 2006, claiming priority based on Japanese Patent Application No. 2005-321798, filed Nov. 7, 2005, the contents of all of which are incorporated herein by reference in their entirety.

TECHNICAL FIELD

The present invention relates to a stable composition containing reduced coenzyme $Q_{10}$ and a method for stabilization of reduced coenzyme $Q_{10}$. The reduced coenzyme $Q_{10}$ shows high oral absorbability as compared with oxidized coenzyme $Q_{10}$ and is a useful compound excellent as a food, food with nutrient function claims, food for specified health use, nutritional supplement, nutritional product, animal drug, drink, feed, cosmetic, pharmaceutical product, therapeutic drug, prophylactic drug and the like.

BACKGROUND ART

It is known that reduced coenzyme $Q_{10}$ can be obtained, for example, by a method comprising producing coenzyme $Q_{10}$ by a conventionally known method such as synthesis, fermentation, extraction from a naturally occurring substance and the like, and concentrating a reduced coenzyme $Q_{10}$ fraction in an eluate from chromatography and the like (see patent reference 1). In this case, the Patent Publication describes that oxidized coenzyme $Q_{10}$ contained in the above-mentioned reduced coenzyme $Q_{10}$ can be reduced with a general reducing agent such as sodium borohydride, sodium hydrosulfite (sodium dithionite) and the like, and concentrated by chromatography, and that the reduced coenzyme $Q_{10}$ can also be obtained by a method comprising reacting highly pure coenzyme $Q_{10}$ containing the existing oxidized type as a main ingredient with the above-mentioned reducing agent.

However, the reduced coenzyme $Q_{10}$ obtained as described above cannot be always obtained at high purity, and tends to be obtained, for example, as a crystal, an oily product or a semi-solid material of low purity containing impurities including oxidized coenzyme $Q_{10}$.

The present inventors have conducted intensive studies, and as a result, they have established a production method for obtaining reduced coenzyme $Q_{10}$ of high quality, and filed a patent application (for example, patent references 2 to 4).

However, reduced coenzyme $Q_{10}$ is easily oxidized by molecular oxygen into oxidized coenzyme $Q_{10}$, and even in a case where reduced coenzyme $Q_{10}$ of high quality is produced by a method as described in the above-mentioned filed patent application, stabilization of reduced coenzyme $Q_{10}$ has been remained as an important issue when it is processed into a food, food with nutrient function claims, food for specified health use, nutritional supplement, nutritional product, animal drug, drink, feed, cosmetic, pharmaceutical product, therapeutic drug, prophylactic drug and the like, or a material or composition therefor, and/or preserved after processing. Complete removal or blocking of oxygen during the above-mentioned processing and preservation is extremely difficult, and remaining or admixed oxygen particularly during heating for processing and long-term preservation exerts a markedly adverse effect. The above-mentioned oxidation is directly related to quality problems such as the by-product oxidized coenzyme $Q_{10}$.

As mentioned above, stabilization of reduced coenzyme $Q_{10}$ (protection from oxidation) is a highly important object. However, since reduced coenzyme $Q_{10}$ is not commercially available to date, the study of methods and compositions for stable retention of reduced coenzyme $Q_{10}$ has not been undertaken very much. As a conventionally method for stably retaining reduced coenzyme $Q_{10}$, a method including addition of a reducing agent is known. However, some of the reducing agents used therefor are not suitable for food and pharmaceutical products, and many of reducing agents did not have sufficient objective stability.

For example, patent reference 5, which discloses a composition concurrently containing a reducing agent and a production method thereof, also discloses 1) a composition comprising reduced coenzyme $Q_{10}$; a reducing agent in an amount effective for eliminating oxidation of reduced coenzyme $Q_{10}$ into oxidized coenzyme $Q_{10}$; a surfactant, vegetable oil or a mixture thereof in an amount effective for dissolving the above-mentioned reduced coenzyme $Q_{10}$ and the above-mentioned reducing agent; and a solvent as necessary, 2) a composition for oral administration wherein the above-mentioned composition is prepared into a gelatin capsule or a tablet, and 3) a method of preparing the above-mentioned composition containing reduced coenzyme $Q_{10}$ in situ using oxidized coenzyme $Q_{10}$ and a reducing agent. However, no detailed description relating to the quality, stabilizing effect and the like of the reduced coenzyme $Q_{10}$ contained in the composition is provided, and the expected level of stabilization is not clear.

In addition, the above-mentioned composition and preparation method thereof are highly complicated and complex since plural roles are conferred to the composition (i.e., firstly, a role as a reaction site for reducing oxidized coenzyme $Q_{10}$ to reduced coenzyme $Q_{10}$, and secondly, a role of stably retaining reduced coenzyme $Q_{10}$). Moreover, the above-mentioned composition and a preparation method thereof are not entirely safe because the reaction mixture is used as it is.

In addition, ascorbic acids to be used as reducing agents are oxidized to produce a considerable amount of dehydroascorbic acids, and the dehydroascorbic acids get mixed in with the above-mentioned composition, posing a problem. Dehydroascorbic acids and oxalic acid produced by decomposition from dehydroascorbic acids are highly noxious, unlike ascorbic acids. For example, an increased amount of lipid peroxide and a decreased amount of antioxidants in the liver and kidney, and an increased amount of oxalic acid in the kidney have been reported, and side effects such as decreased resistance to oxidation stress, easy onset of ureteral lithiasis (non-patent reference 1) and the like are feared.

The present inventors considered that the above-mentioned problems have been solved, and have reported a composition which does not substantially inhibit stabilization of reduced coenzyme $Q_{10}$ and contains reduced coenzyme $Q_{10}$, fats and oils other than olive oil and/or a polyol, and if necessary, a polyglycerin fatty acid ester (patent reference 6), but the method does not always provide sufficient oxidative stability in a condition where further oxidative stability is required for long-term preservation or under a bad condition, and the like.

Patent reference 1: JP-A-10-109933
Patent reference 2: WO 03/06408
Patent reference 3: WO 03/06409
Patent reference 4: WO 03/32967

Patent reference 5: WO 01/52822
Patent reference 6: WO 03/062182
Non-patent reference 1: Nutriton Research, vol. 13, pp. 667-676, 1993
Background Art

DISCLOSURE OF THE INVENTION

Summary of the Invention

The present invention has been done in view of the aforementioned circumstance, and it is an object to provide a preferable composition and a simple method in which reduced coenzyme $Q_{10}$ can be stably retained by protection from oxidation when a reduced coenzyme $Q_{10}$-containing composition is preserved as it is, or when it is processed into and/or preserved as food, food with nutrient function claims, food for specified health use, nutritional supplement, nutritional product, animal drug, drink, feed, cosmetic, pharmaceutical product, therapeutic drug, prophylactic drug and the like.

Means of Solving the Invention

The present inventors have conducted intensive studies in an attempt to solve the above-mentioned problems, and as a result, have found that ingredients so far reported for preparation of food, food with nutrient function claims, food for specified health use, nutritional supplement, nutritional product, animal drug, drink, feed, cosmetic, pharmaceutical product, therapeutic drug, prophylactic drug and the like do not always preferably act for stabilization of reduced coenzyme $Q_{10}$ (i.e., protection from oxidation), that even if a complicated and complex composition is not prepared, reduced coenzyme $Q_{10}$ is surprisingly preferably protected from oxidation by molecular oxygen under the coexistence with a propylene glycol fatty acid ester, and that a propylene glycol fatty acid ester is suitable also as a solvent for dissolving reduced coenzyme $Q_{10}$.

That is, the present invention relates to a method for stabilization of reduced coenzyme $Q_{10}$ characterized by concurrently containing a propylene glycol fatty acid ester in a composition containing reduced coenzyme $Q_{10}$.

In addition, the present invention relates to a reduced coenzyme Q10-containing composition containing reduced coenzyme Q10 and a propylene glycol fatty acid ester.

DETAILED DESCRIPTION OF THE INVENTION

Effect of the Invention

According to the present invention, a reduced coenzyme $Q_{10}$-containing composition which is stable against and suitable for oxidation especially without adding a plurality of ingredients, and a method for stabilization of reduced coenzyme $Q_{10}$ can be provided.

BEST MODE FOR CARRYING OUT THE INVENTION

The present invention is explained in detail below.

In the present invention, in order to inhibit oxidation (protect oxidation) of reduced coenzyme $Q_{10}$ by molecular oxygen into oxidized coenzyme $Q_{10}$, a propylene glycol fatty acid ester is allowed to be concurrently contained in a composition containing reduced coenzyme $Q_{10}$. That is, a composition which is stable against oxidation can be obtained only by producing a composition containing reduced coenzyme $Q_{10}$ and a propylene glycol fatty acid ester as essential constituting ingredients.

In the present invention, reduced coenzyme $Q_{10}$ may be single reduced coenzyme $Q_{10}$ or coenzyme $Q_{10}$ that is a mixture of oxidized coenzyme $Q_{10}$ and reduced coenzyme $Q_{10}$. When coenzyme $Q_{10}$ is the mixture, a weight ratio of reduced coenzyme $Q_{10}$ to the total amount of coenzyme $Q_{10}$ (that is, the total amount of reduced coenzyme $Q_{10}$ and oxidized coenzyme $Q_{10}$) is not particularly limited, but is, for example, not less than 20 wt %, usually not less than 40 wt %, preferably not less than 60 wt %, more preferably not less than 80 wt %, particularly preferably not less than 90 wt %, and most preferably not less than 96 wt %. The upper limit is 100 wt %, and is not particularly limited, but usually not more that 99.9 wt %. Hereinafter, a case where coenzyme $Q_{10}$ is only shown in the present specification refers to both cases of a mixture of oxidized coenzyme $Q_{10}$ and reduced coenzyme $Q_{10}$, and single reduced coenzyme $Q_{10}$.

In the present invention, as a propylene glycol fatty acid ester, both of a propylene glycol fatty acid monoester and a propylene glycol fatty acid diester can be preferably used. As a fatty acid residue of a propylene glycol fatty acid ester, irrespective of whether it is saturated or unsaturated, a propylene glycol fatty acid ester comprising various fatty acid residues can be used, but a propylene glycol fatty acid ester with a fatty acid residue having 8 to 18 carbon atoms is particularly preferably used.

Examples of the above-mentioned fatty acid residue include one or more kinds of fatty acid residues selected from the group consisting of caprylic acid, capric acid, lauric acid, myristic acid, palmitic acid, stearic acid, isostearic acid, oleic acid, linoleic acid, linolenic acid and the like.

Such a propylene glycol fatty acid ester is not particularly limited. Propylene glycol monocaprylate, propylene glycol dicaprylate, propylene glycol monocaprate, propylene glycol dicaprate, propylene glycol monolaurate, propylene glycol dilaurate, propylene glycol monomyristate, propylene glycol dimyristate, propylene glycol monopalmitate, propylene glycol dipalmitate, propylene glycol monostearate, propylene glycol distearate, propylene glycol monoisostearate, propylene glycol diisostearate, propylene glycol monooleate, propylene glycol dioleate, propylene glycol monolinoleate, propylene glycol dilinoleate, propylene glycol monolinolenate, propylene glycol dilinolenate and the like can be used as a propylene glycol fatty acid ester. In addition, a propylene glycol fatty acid diester having two different fatty acid residues other than the above-mentioned propylene glycol fatty acid esters may be used.

Among the above-mentioned propylene glycol fatty acid esters, propylene glycol monocaprylate, propylene glycol dicaprylate, propylene glycol monocaprate, propylene glycol dicaprate, propylene glycol monolaurate, propylene glycol dilaurate, propylene glycol monopalmitate, propylene glycol dipalmitate, propylene glycol monostearate, propylene glycol distearate, propylene glycol monooleate, propylene glycol dioleate and the like are preferred from the viewpoint of handleability or the like.

In addition, preferable propylene glycol fatty acid esters are those that are acceptable for food or pharmaceutical products.

Each of the above-mentioned propylene glycol fatty acid esters can be used alone or as a mixture thereof.

In the above-mentioned propylene glycol fatty acid esters, solubility of reduced coenzyme $Q_{10}$ is higher than those of fats and oils described later. When a composition having reduced coenzyme $Q_{10}$ dissolved therein is desired, as compared with fats and oils or the like, there is also an advantage that the propylene glycol fatty acid esters are easily used also as a medium (solvent) for dissolving reduced coenzyme $Q_{10}$ (or a mixture of reduced coenzyme $Q_{10}$ and oxidized coenzyme $Q_{10}$) and thus eliminate the need for other solvents (for example, fats and oils), or that a composition in which reduced coenzyme $Q_{10}$ is dissolved and contained at a concentration higher than that in another solvent can be produced. Further, it can also be anticipated that absorbability of reduced coenzyme $Q_{10}$ into the body is enhanced by using the propylene glycol fatty acid ester as a medium for dissolving reduced coenzyme $Q_{10}$.

That is, in an aspect of the present invention, there is provided a composition containing reduced coenzyme $Q_{10}$ and the above-mentioned propylene glycol fatty acid ester as main ingredients. Generally, although the above-mentioned composition is preferably a liquid composition in which reduced coenzyme $Q_{10}$ is dissolved or suspended in the propylene glycol fatty acid ester, the composition may be in a solid or slurry form depending on a kind of a propylene glycol fatty acid ester to be used.

It is needless to say that the simplest constitution of the present invention is a composition consisting of a propylene glycol fatty acid ester and reduced coenzyme $Q_{10}$, but in the present invention, it is acceptable to add other ingredients which do not substantially inhibit stabilization of reduced coenzyme $Q_{10}$, and it is also acceptable to add other ingredients, even if they inhibit stabilization of reduced coenzyme $Q_{10}$, as long as they are added in such an amount that the stabilization is not substantially inhibited. In addition, such ingredients will exist in large numbers. From this viewpoint, the essence of the present invention is to produce a composition containing a propylene glycol fatty acid ester and reduced coenzyme $Q_{10}$, which does not substantially inhibit the stabilization of reduced coenzyme $Q_{10}$, and in the present invention, there is no hindrance in containing other ingredients which do not substantially inhibit stabilization of reduced coenzyme $Q_{10}$. Examples of such ingredients include fats and oils, surfactants other than propylene glycol fatty acid esters, ethanol, water and the like.

The above-mentioned fats and oils may be natural fats and oils derived from animals and plants, or may be synthetic fats and oils or processed fats and oils. Examples of the vegetable fats and oils include coconut oil, palm oil, palm kernel oil, linseed oil, camellia oil, brown rice germ oil, olive oil, rapeseed oil, rice oil, peanuts oil, corn oil, wheat germ oil, soybean oil, perilla oil, cottonseed oil, sunflower seed oil, kapok oil, evening primrose oil, shea butter, sal butter, cacao butter, sesame oil, safflower oil and the like, and examples of animal fats and oils include lard, milk fat, fish oil, beef fat and the like. Furthermore, fats and oils obtained by processing them by fractionation, hydrogenation, transesterification (e.g., hydrogenated oil) and the like also can be used. Medium-chain triglyceride (MCT), partial glyceride of fatty acid, phospholipid and the like can also be used.

Examples of medium-chain triglyceride include triglyceride wherein the fatty acid has 6 to 12 carbon atoms, preferably 8 to 12 carbon atoms. Examples of partial glyceride of fatty acid include monoglyceride and diglycerides wherein the fatty acid has 6 to 18 carbon atoms, preferably 6 to 12 carbon atoms.

The phospholipid is not particularly limited. For example, lecithin (yolk lecithin, refined soybean lecithin etc.), lysolecithin, phosphatidylcholine, phosphatidylethanolamine, phosphatidylserine, sphingomyelin, dicetyl phosphoric acid, stearyl amine, phosphatidyl glycerol, phosphatidic acid, phosphatidyl inositol amine, cardiolipin, ceramide phosphorylethanolamine, and ceramide phosphorylglycerol, mixtures thereof and the like can be used as a phospholipid.

Of the above-mentioned fats and oils, vegetable fats and oils, synthetic fats and oils and processed fats and oils are preferable from the aspects of handleability, odor and the like. In addition, fats and oils acceptable for food or pharmaceutical products are preferred. Fats and oils are preferably selected in consideration of the price of fats and oils, stability of reduced coenzyme $Q_{10}$, solubility of coenzyme $Q_{10}$ and the like further. For example, coconut oil, palm oil, palm kernel oil, olive oil, rapeseed oil, rice oil, soybean oil, cottonseed oil, MCT, phospholipid and the like are preferred, and rice oil, soybean oil, rapeseed oil, MCT, phospholipid and the like are particularly preferred. From the aspect of the solubility of coenzyme $Q_{10}$, MCT can be particularly preferably used.

Examples of the above-mentioned surfactant other than a propylene glycol fatty acid ester include a glycerin fatty acid ester, an organic acid monoglyceride, a sucrose fatty acid ester, a condensed ricinoleic acid polyglyceride, a sorbitan fatty acid ester, a polyoxyethylene sorbitan fatty acid ester and the like.

The glycerin fatty acid ester is not particularly limited and both of a monoglycerin fatty acid ester and a polyglycerin fatty acid ester can be used, but the degree of polymerization of glycerin is preferably not more than 10. As a fatty acid residue in a glycerin fatty acid ester, irrespective of whether it is saturated or unsaturated, a glycerin fatty acid ester having various fatty acid residues can be used, but the fatty acid residue is not particularly limited. Furthermore, a glycerin fatty acid ester wherein the fatty acid residue has not less than 8 and not more than 18 carbon atoms is preferred.

The organic acid monoglyceride is not particularly limited. For example, acetic acid monoglyceride, lactic acid monoglyceride, citric acid monoglyceride, diacetyl tartaric acid monoglyceride, succinic acid monoglyceride and the like can be used as a organic acid monoglyceride.

The sucrose fatty acid ester is not particularly limited. For example, sucrose stearate, sucrose isostearate, sucrose palmitate, sucrose myristate, sucrose oleate, sucrose laurate, sucrose behenate, sucrose erucate and the like can be used as a sucrose fatty acid ester. The above-mentioned sucrose fatty acid esters can be used irrespective of whether they are monoesters or polyesters. It is needless to say that a mixed fatty acid ester having a plurality of fatty acid residues may be used.

The condensed ricinoleic acid polyglyceride is not particularly limited. For example, condensed ricinoleic acid monoglyceride, condensed ricinoleic acid diglyceride, condensed ricinoleic acid triglyceride, condensed ricinoleic acid tetraglyceride, condensed ricinoleic acid pentaglyceride, condensed ricinoleic acid hexaglyceride, condensed ricinoleic acid octaglyceride and the like can be used as a condensed ricinoleic acid polyglyceride. Condensed ricinoleic acid tetraglyceride, condensed ricinoleic acid hexaglyceride and the like are preferably used.

The sorbitan fatty acid ester is not particularly limited. For example, sorbitan stearate, sorbitan isostearate, sorbitan palmitate, sorbitan myristate, sorbitan oleate, sorbitan laurate, sorbitan behenate, sorbitan erucate and the like can be used as a sorbitan fatty acid ester. The above-mentioned sorbitan fatty acid esters can be used irrespective of whether they are monoesters or polyesters. It is needless to say that a mixed fatty acid ester having a plurality of fatty acid residues may be used.

The polyoxyethylene sorbitan fatty acid ester is not particularly limited. For example, polyoxyethylene sorbitan stearate, polyoxyethylene sorbitan isostearate, polyoxyethylene sorbitan palmitate, polyoxyethylene sorbitan myristate, polyoxyethylene sorbitan oleate, polyoxyethylene sorbitan laurate, polyoxyethylene sorbitan behenate, polyoxyethylene sorbitan erucate and the like can be used as a polyoxyethylene sorbitan fatty acid ester. The above-mentioned polyoxyethylene sorbitan fatty acid esters can be used irrespective of whether they are monoesters or polyesters. It is needless to say that a mixed fatty acid ester having a plurality of fatty acid residues may be used.

In addition, among the above-mentioned surfactants, those that are acceptable for food or pharmaceutical products are preferred.

The content of the above-mentioned fats and oils and surfactant other than propylene glycol fatty acid esters in a composition is not particularly limited and can be appropriately set in consideration of price, handleability and the like. However, the lower limit is usually not less than about 1 wt %, preferably not less than about 3 wt %, more preferably not less than about 5 wt %, and particularly preferably not less than about 10 wt %. The upper limit is usually not more than about 90 wt %, preferably not more than about 70 wt %, more preferably not more than about 60 wt %, and particularly preferably not more than about 30 wt %, and most preferably not more than about 20 wt %. However, the content other than the above-mentioned contents can also be used, if necessary. It is also needless to say that there is no problem even if two or more kinds of the above-mentioned fats and oils or the above-mentioned surfactants are used.

In addition, in the present invention, there is no hindrance in further adding other pharmaceutically acceptable ingredients to a composition containing a propylene glycol fatty acid ester and reduced coenzyme $Q_{10}$. Such a substance is not particularly limited. For example, an excipient, a disintegrant, a lubricant, a binder, an antioxidant, a coloring agent, an anticoagulant, an absorption promoter, a solubilizing agent for an active ingredient, a stabilizer, a viscosity modifier and the like can be used as such a substance. It is needless to say that there is no hindrance in concurrently containing other active ingredients except coenzyme $Q_{10}$ in the composition.

The above-mentioned excipient is not particularly limited. For example, sucrose, lactose, glucose, cornstarch, mannitol, crystalline cellulose, calcium phosphate, calcium sulfate and the like can be used as an excipient.

The above-mentioned disintegrant is not particularly limited. For example, starch, agar, calcium citrate, calcium carbonate, sodium hydrogencarbonate, dextrin, crystalline cellulose, carboxymethylcellulose, tragacanth and the like can be used as a disintegrant.

The above-mentioned lubricant is not particularly limited. For example, talc, magnesium stearate, polyethylene glycol, silica, hydrogenated vegetable oil and the like can be used as a lubricant.

The above-mentioned binder is not particularly limited. For example, ethylcellulose, methylcellulose, hydroxypropylmethylcellulose, tragacanth, shellac, gelatin, gum arabic, polyvinylpyrrolidone, polyvinyl alcohol, polyacrylic acid, polymethacrylic acid, sorbitol and the like can be used as a binder.

The above-mentioned antioxidant is not particularly limited. For example, ascorbic acid and derivatives thereof, tocopherol and derivatives thereof, vitamin A and derivatives thereof, β-carotin, sodium hydrogen sulfite, sodium thiosulfate, sodium pyrosulfite, citric acid and derivatives thereof, and the like can be used as an antioxidant.

The above-mentioned coloring agent is not particularly limited. For example, those allowed to be added to pharmaceutical products and food and the like can be used as a coloring agent.

The above-mentioned anticoagulant is not particularly limited. For example, stearic acid, talc, light anhydrous silicic acid, water-containing silicon dioxide and the like can be used as an anticoagulant.

The above-mentioned absorption promoter is not particularly limited. For example, higher alcohols, higher fatty acids, the above-mentioned surfactants and the like can be used as an absorption promoter.

The above-mentioned solubilizing agent for active ingredient is not particularly limited. For example, organic acids such as fumaric acid, succinic acid, malic acid and the like, and the like can be used as a dissolution agent.

The above-mentioned stabilizer is not particularly limited. For example, benzoic acid, sodium benzoate, ethyl paraoxybenzoate and the like can be used as a stabilizer.

The above-mentioned viscosity modifier is not particularly limited. For example, beeswax, carnauba wax, candelilla wax, rice bran wax, sugarcane wax, shellac wax, jojoba wax and the like can be used as a viscosity modifier. Beeswax, carnauba wax and rice bran wax are preferably used, and beeswax is particularly preferably used.

The above-mentioned other active ingredients except coenzyme $Q_{10}$ are not particularly limited. For example, amino acids, vitamins such as vitamin C and vitamin E and derivatives thereof, carotenoids such as β-carotin and astaxanthin, minerals, polyphenols, organic acids, saccharides, peptides, proteins and the like can be used as other active ingredients except coenzyme $Q_{10}$.

In the present invention, the content of reduced coenzyme $Q_{10}$ in the composition is not particularly limited, but is, for example, usually not less than about 1 wt %, preferably not less than about 3 wt %, more preferably not less than about 5 wt %, still more preferably not less than about 8 wt %, and particularly preferably not less than about 10 wt %, in consideration of stability of reduced coenzyme $Q_{10}$, ease and convenience of use thereof, and the like. Further, the upper limit of the content of reduced coenzyme $Q_{10}$ in the composition is not particularly limited, but is usually not more than about 50 wt %, preferably not more than about 40 wt %, and more preferably not more than about 30 wt %, in consideration of a liquid state of the composition and the like.

In addition, in the present invention, the content of a propylene glycol fatty acid ester in the composition is not particularly limited, but is, for example, usually not less than about 5 wt %, preferably not less than about 10 wt %, more preferably not less than about 15 wt %, particularly preferably not less than about 20 wt %, and still more preferably not less than about 30 wt %, in consideration of stabilizing effect on and solubility in reduced coenzyme $Q_{10}$, and the like. Further, the upper limit of the content of a propylene glycol fatty acid ester in the composition is not particularly limited, but is, for example, usually about 99 wt %, preferably about 95 wt %, and more preferably about 90 wt %.

Further, in the present invention, the reduced coenzyme $Q_{10}$ in the composition may be externally added or may be reduced coenzyme $Q_{10}$ obtained by reducing oxidized coenzyme $Q_{10}$ in a composition containing the above-mentioned propylene glycol fatty acid ester using a reducing agent such as sodium hydrosulfite (sodium dithionite) and ascorbic acid. Typically, the reduced coenzyme $Q_{10}$ is preferably externally added because ingredients of the composition can be simplified and easily prepared.

The reduced coenzyme $Q_{10}$-containing composition of the present invention can also be used as it is, but one obtained by processing the composition into an oral administration form such as capsules (hard capsule, soft capsule, microcapsule), tablets, powder, chewable tablets, syrups, drinks and the like can also be preferably used, and one obtained by processing the composition into a form for external preparation or quasi-drugs such as cream, suppository, toothpaste and the like can also be used. Particularly preferable processing form is a capsule, and a soft capsule is most preferably used. A capsule base material in this case is not particularly limited, and other base materials (for example, viscosity increasing stabilizers of seaweed-derived products such as carrageenan and alginic acid, vegetable seed-derived products such as locust bean gum and guar gum, and the like, and cellulose-containing agents for production, which are usable also as a food additive) including gelatin derived from beef bones, cattle skin, pig skin, fish skin and the like, can also be used.

In order to exert the effect of the present invention at a maximum, for example, the reduced coenzyme $Q_{10}$-containing composition of the present invention is preferably prepared and/or preserved under a deoxidation atmosphere. In addition, the above-mentioned processing into various forms and preservation after processing are also preferably performed under a deoxidation atmosphere. The deoxidation atmosphere can be achieved by replacement by an inert gas, decompression, boiling or using them in combination. It is preferred that the replacement by an inert gas, that is, an inert gas atmosphere is at least used. Examples of the inert gas include nitrogen gas, helium gas, argon gas, hydrogen gas and carbon dioxide gas, and nitrogen gas is preferred.

As described above, a propylene glycol fatty acid ester is allowed to be concurrently contained in a composition containing reduced coenzyme $Q_{10}$ to produce a composition containing reduced coenzyme $Q_{10}$ and a propylene glycol fatty acid ester as essential constituting ingredients, and if necessary, the composition is processed into an oral administration form, and thereby it can be expected that the retention rate of reduced coenzyme $Q_{10}$ is maintained at not less than about 90 wt %, preferably not less than about 95 wt % after being preserved a predetermined period of time. Further, the term, retention rate, referred herein is determined as a rate of an absolute amount (or concentration) of reduced coenzyme $Q_{10}$ in the composition after being preserved for a predetermined period of time/an absolute amount (or concentration) of reduced coenzyme $Q_{10}$ in the composition before being preserved. The above-mentioned preservation period is, for example, not less than 1 day, preferably not less than 1 week, more preferably not less than 1 month, particularly preferably not less than 6 months, particularly more preferably not less than 1 year, and most preferably not less than 2 years.

The term "stabilization" in the present invention (or "stable composition") refers to the fact that reduced coenzyme $Q_{10}$ is more protected from oxidation as compared with other methods or preservation in other compositions to thereby increase the retention rate (or a composition having increased retention rate), and is not particularly limited, but is, for example, the fact that the above-mentioned retention rate is maintained during the above-mentioned preservation period (or maintainable composition). As an example, the retention rate of reduced coenzyme $Q_{10}$ after being preserved in air at 40° C. for 2 weeks is not less than about 80%, preferably not less than about 85%, and more preferably not less than about 90%.

According to the present invention, reduced coenzyme $Q_{10}$ can be preferably protected from oxidation, and a composition free of an oxidation product of a reducing agent such as dehydroascorbic acids and the like can be provided. Moreover, a composition showing high biological absorbability of reduced coenzyme $Q_{10}$ can also be provided.

EXAMPLES

The present invention is explained in more detail in the following by referring to Examples, which are not to be construed as limitative.

In Examples, the purity of reduced coenzyme $Q_{10}$, and the weight ratio of reduced coenzyme $Q_{10}$ and oxidized coenzyme $Q_{10}$ were determined by HPLC analysis as discussed below. However, the purity of the obtained reduced coenzyme $Q_{10}$ does not define the limit value of the purity in the present invention. Likewise, the weight ratio of reduced coenzyme $Q_{10}$ and oxidized coenzyme $Q_{10}$ does not either define the upper limit value of the weight ratio of reduced coenzyme $Q_{10}$ to coenzyme $Q_{10}$.

(HPLC Analysis Conditions)
column: SYMMETRY C18 (manufactured by Waters) 250 mm (length) 4.6 mm (inner diameter), mobile phase; $C_2H_5OH:CH_3OH=4:3$ (v:v), detection wavelength; 210 nm, flow rate; 1 ml/min, retention time of reduced coenzyme $Q_{10}$; 9.1 min, retention time of oxidized coenzyme $Q_{10}$; 13.3 min.

Production Example 1

Oxidized coenzyme $Q_{10}$ (100 g, purity 99.4%) and L-ascorbic acid (60 g) were added to 1000 g of ethanol, and the mixture was stirred at 78° C. to perform a reduction reaction. After 30 hr, the mixture was cooled to 50° C., and 400 g of ethanol was added while maintaining at the same temperature. The ethanol solution (containing 100 g of reduced coenzyme $Q_{10}$) was cooled to 2° C. at a cooling rate of 10° C./hr with stirring to give a white slurry. The obtained slurry was filtered under reduced pressure, the wet crystals were washed with cold ethanol, cold water and cold ethanol in this order (temperature of cold solvent used for washing, 2° C.) and dried under reduced pressure (20-40° C., 1-30 mmHg) to give white dry crystals (95 g, isolated product yield 95 mol %). All operations except reduced-pressure drying were performed under a nitrogen atmosphere. The weight ratio of reduced coenzyme $Q_{10}$/oxidized coenzyme $Q_{10}$ of the obtained crystals was 99.5/0.5, and the purity of reduced coenzyme $Q_{10}$ was 99.2%.

Example 1

The reduced coenzyme $Q_{10}$ (0.3 g) obtained in Production Example 1 was added to and mixed with 10 g of each propylene glycol fatty acid ester described in Table 1, and the mixture was preserved in air at 40° C. The weight ratio of the reduced coenzyme $Q_{10}$/oxidized coenzyme $Q_{10}$ after the lapse of 2 weeks is shown in Table 1. The crystals of the reduced coenzyme $Q_{10}$ obtained in Production Example 1 were preserved as it was in the same condition for 3 days, and the result is also shown together.

TABLE 1

| Propylene glycol fatty acid ester | R |
|---|---|
| Propylene glycol dioleate | 97.2/2.8 |
| Propylene glycol dicaprylate | 96.9/3.1 |
| Crystals | 75.0/25.0 |

R: Weight ratio of the reduced coenzyme $Q_{10}$/oxidized coenzyme $Q_{10}$

Example 2

The reduced coenzyme $Q_{10}$ (0.3 g) obtained in Production Example 1 was added to and mixed with 10 g of a mixture of each propylene glycol fatty acid ester and each fat and oil (weight ratio of each propylene glycol fatty acid ester and each fat and oil: 5/5) shown in Table 2, and the mixture was preserved in air at 40° C. The weight ratio of reduced coenzyme $Q_{10}$/oxidized coenzyme $Q_{10}$ after the lapse of 2 weeks is shown in Table 2.

TABLE 2

| Propylene glycol fatty acid ester | Fat and oil | R |
|---|---|---|
| propylene glycol monooleate | MCT | 96.2/3.8 |
| Propylene glycol monocaprylate | MCT | 95.9/4.1 |
| Propylene glycol dioleate | MCT | 97.1/2.9 |
| Propylene glycol dicaprylate | MCT | 97.4/2.6 |
| propylene glycol monooleate | Rapeseed oil | 95.5/4.5 |
| Propylene glycol dicaprylate | Rapeseed oil | 96.9/3.1 |

R: Weight ratio of the reduced coenzyme $Q_{10}$/oxidized coenzyme $Q_{10}$

Example 3

The reduced coenzyme $Q_{10}$ (0.3 g) obtained in Production Example 1 was added to and mixed with 10 g of a mixture of propylene glycol monocaprylate and MCT (the weight ratio is described in Table 3), and the mixture was preserved in air at 40° C. The weight ratio of reduced coenzyme $Q_{10}$/oxidized coenzyme $Q_{10}$ after the lapse of 2 weeks is shown in Table 3.

TABLE 3

| Weight ratio of propylene glycol monocaprylate/MCT | R |
|---|---|
| 30/70 | 96.4/3.6 |
| 50/50 | 96.2/3.8 |
| 70/30 | 96.7/3.3 |

R: Weight ratio of the reduced coenzyme $Q_{10}$/oxidized coenzyme $Q_{10}$

Example 4, Comparative Example 1

The reduced coenzyme $Q_{10}$ (0.3 g) obtained in Production Example 1 was added to and mixed with 10 g of a mixture of medium-chain triglyceride (MCT, 8 (number of carbon atoms):10 (number of carbon atoms)=6:4) and each surfactant shown in Table 4 (the weight ratio is described in Table 4), and the mixture was preserved in air at 40° C. The weight ratio of reduced coenzyme $Q_{10}$/oxidized coenzyme $Q_{10}$ after the lapse of a predetermined period is shown in Table 4.

TABLE 4

| Surfactants | Weight ratio of MCT/surfactant | R | Preservation period |
|---|---|---|---|
| Propylene glycol dicaprylate | 7/3 | 98.5/1.5 | 5 days |
| Diglycerin monooleate | 7/3 | 90.4/9.6 | 5 days |
| Condensed ricinoleic acid tetraglyceride | 7/3 | 33.3/66.7 | 5 days |
| Condensed ricinoleic acid hexaglyceride | 7/3 | 43.2/56.8 | 5 days |
| Polyoxyethylene sorbitan monooleate (Tween80) | 9/1 | 30.5/69.5 | 3 days |
| Sorbitan monooleate (Span80) | 9/1 | 56.6/43.4 | 3 days |

R: Weight ratio of the reduced coenzyme $Q_{10}$/oxidized coenzyme $Q_{10}$

Example 5, Comparative Example 2

The reduced coenzyme $Q_{10}$ (0.3 g) obtained in Production Example 1 was added to 10 g of each propylene glycol fatty acid ester or each fat and oil shown in Table 5, and the mixture was preserved in air at 40° C. The weight ratio of reduced coenzyme $Q_{10}$/oxidized coenzyme $Q_{10}$ after the lapse of 7 days is shown in Table 5.

TABLE 5

| Fat and oil or propylene glycol fatty acid ester | R |
|---|---|
| Propylene glycol dicaprylate | 98.3/1.7 |
| Medium-chain triglyceride (MCT, 8 (number of carbon atoms): 10 (number of carbon atoms) = 6/4) | 96.1/3.9 |
| Rapeseed oil | 95.7/4.3 |

R: Weight ratio of the reduced coenzyme $Q_{10}$/oxidized coenzyme $Q_{10}$

As described above, it can be seen from the results of Examples 1 to 5 and Comparative Examples 1 and 2 that reduced coenzyme $Q_{10}$ is stably preserved against oxidation by concurrently containing a propylene glycol fatty acid ester and that a stabilizing effect of a propylene glycol fatty acid ester on reduced coenzyme $Q_{10}$ is superior to that of generally used fat and oil or another surfactant.

Reference Example 1

The crystals obtained in Production Example 1 were used to examine the solubility of reduced coenzyme $Q_{10}$ in propylene glycol monocaprylate, propylene glycol dicaprylate, medium-chain triglyceride (MCT, 8 (number of carbon atoms):10 (number of carbon atoms)=6:4), soybean oil or rapeseed oil at 30° C. The results are shown in Table 6.

TABLE 6

|  | Solubility (w/w %) |
|---|---|
| Propylene glycol monocaprylate | 32.3 |
| Propylene glycol dicaprylate | 38.5 |
| Medium-chain triglyceride | 22.4 |
| Soybean oil | 10.9 |
| Rapeseed oil | 10.7 |

It can be seen from the results described above that a propylene glycol fatty acid ester shows solubility in reduced coenzyme $Q_{10}$ higher than that of fat and oil (specially MCT, that is preferably used because of showing extremely high solubility among fats and oils) conventionally used for dissolving reduced coenzyme $Q_{10}$, and is thus excellent also as a medium for dissolving reduced coenzyme $Q_{10}$.

Preparation Example 1

The crystals obtained in Production Example 1 were added to propylene glycol dicaprylate at 50° C. and a soft capsule preparation of gelatin made of the following ingredients was obtained by a conventional method.

| Reduced coenzyme $Q_{10}$ | 100 parts by weight |
|---|---|
| Propylene glycol dicaprylate | 900 parts by weight |

Preparation Example 2

The crystals obtained in Production Example 2 were added to a mixture of propylene glycol monocaprate and medium-chain triglyceride at 50° C. and a soft capsule preparation of gelatin made of the following ingredients was obtained by a conventional method.

| | |
|---|---|
| Reduced coenzyme $Q_{10}$ | 60 parts by weight |
| Propylene glycol monocaprate | 440 parts by weight |
| Medium-chain triglyceride | 500 parts by weight |

Preparation Example 3

The crystals obtained in Production Example 1 were added to a mixture of propylene glycol monocaprylate, medium-chain triglyceride, hydrogenated oil, beeswax and lecithin at 50° C. and a soft capsule preparation of gelatin made of the following ingredients was obtained by a conventional method.

| | |
|---|---|
| Reduced coenzyme $Q_{10}$ | 100 parts by weight |
| Propylene glycol monocaprylate | 400 parts by weight |
| Medium-chain triglyceride | 350 parts by weight |
| Hydrogenated oil | 70 parts by weight |
| Beeswax | 60 parts by weight |
| Lecithin | 20 parts by weight |

Preparation Example 4

The crystals obtained in Production Example 1 were added to a mixture of propylene glycol monocaprate, rapeseed oil, hydrogenated oil, beeswax and lecithin at 50° C. and a soft capsule preparation of gelatin made of the following ingredients was obtained by a conventional method.

| | |
|---|---|
| Reduced coenzyme $Q_{10}$ | 100 parts by weight |
| Propylene glycol monocaprate | 400 parts by weight |
| Rapeseed oil | 350 parts by weight |
| Hydrogenated oil | 70 parts by weight |
| Beeswax | 60 parts by weight |
| Lecithin | 20 parts by weight |

Preparation Example 5

The crystals obtained in Production Example 1 and L-ascorbyl palmitate were added to a mixture of propylene glycol monooleate, medium-chain triglyceride, hydrogenated oil, beeswax and lecithin at 50° C. and a soft capsule preparation of gelatin made of the following ingredients was obtained by a conventional method.

| | |
|---|---|
| Reduced coenzyme $Q_{10}$ | 100 parts by weight |
| L-Ascorbyl palmitate | 100 parts by weight |
| Propylene glycol monooleate | 320 parts by weight |
| Medium-chain triglyceride | 350 parts by weight |
| Hydrogenated oil | 60 parts by weight |
| Beeswax | 50 parts by weight |
| Lecithin | 20 parts by weight |

The invention claimed is:

1. A method for stabilization of reduced coenzyme $Q_{10}$ against oxidation, comprising providing a reduced coenzyme $Q_{10}$-containing composition containing reduced coenzyme $Q_{10}$ and a propylene glycol fatty acid ester, wherein the retention rate of reduced coenzyme $Q_{10}$ after being preserved in air at 40° C. for 2 weeks is not less than 80 wt %, by mixing a propylene glycol fatty acid ester with reduced coenzyme $Q_{10}$ to prepare a composition which protects reduced coenzyme $Q_{10}$ from oxidation,
wherein a fatty acid residue of the propylene glycol fatty acid ester is one or more fatty acid residues selected from the group consisting of caprylic acid, capric acid, lauric acid, myristic acid, palmitic acid, stearic acid, isostearic acid, oleic acid, linoleic acid and linolenic acid, and
wherein the amount of propylene glycol fatty acid ester in the composition is not less than 20 wt % and the amount of reduced coenzyme $Q_{10}$ in the composition is not more than 40 wt %.

2. The method for stabilization of reduced coenzyme $Q_{10}$ of claim 1, wherein the propylene glycol fatty acid ester is acceptable for food or a pharmaceutical product.

3. The method for stabilization of reduced coenzyme $Q_{10}$ of claim 1, wherein the composition further comprises a fat or oil.

4. The method for stabilization of reduced coenzyme $Q_{10}$ of claim 3, wherein the fat or oil is one or more selected from the group consisting of: coconut oil, palm oil, palm kernel oil, linseed oil, camellia oil, brown rice germ oil, olive oil, rapeseed oil, rice oil, peanut oil, corn oil, wheat germ oil, soybean oil, perilla oil, cottonseed oil, sunflower seed oil, kapok oil, evening primrose oil, shea butter, sal butter, cacao butter, sesame oil, safflower oil, lard, milk fat, fish oil, beef fat, a fat or oil obtained by hydrogenation or transesterification, a medium-chain triglyceride, a partial glyceride of a fatty acid, and phospholipids.

5. The method for stabilization of reduced coenzyme $Q_{10}$ of claim 1, wherein the method further comprises providing a surfactant other than a propylene glycol fatty acid ester in the composition.

6. The method for stabilization of reduced coenzyme $Q_{10}$ of claim 5, wherein the surfactant is one or more selected from the group consisting of a glycerin fatty acid ester, an organic acid monoglyceride, a sucrose fatty acid ester, a condensed ricinoleic acid polyglyceride, a sorbitan fatty acid ester, and a polyoxyethylene sorbitan fatty acid ester.

7. The method for stabilization of reduced coenzyme $Q_{10}$ according to claim 3, wherein the fat or oil and/or the surfactant are/is acceptable for food or a pharmaceutical product.

8. The method for stabilization of reduced coenzyme $Q_{10}$ of claim 1, further comprising incorporating an active ingredient that is not reduced coenzyme $Q_{10}$ in the composition.

9. The method for stabilization of reduced coenzyme $Q_{10}$ of claim 1, wherein the content of reduced coenzyme $Q_{10}$ in the composition is not less than 1 wt %.

10. The method for stabilization of reduced coenzyme $Q_{10}$ of claim 1, wherein the reduced coenzyme $Q_{10}$ is prepared in the absence of the propylene glycol fatty acid ester and then mixed with the propylene glycol fatty acid ester.

11. The method for stabilization of reduced coenzyme $Q_{10}$ of claim 1, wherein the composition is prepared or preserved under an inert gas atmosphere.

12. The method for stabilization of the reduced coenzyme $Q_{10}$ of claim 1, wherein said retention rate of reduced coenzyme $Q_{10}$ is not less than 90 wt %.

13. The method according to claim 1, wherein the propylene glycol fatty acid ester is one or more selected from the group consisting of propylene glycol monooleate, propylene glycol monocaprylate, propylene glycol dioleate and propylene glycol dicaprylate.

14. A reduced coenzyme $Q_{10}$-containing composition, containing reduced coenzyme $Q_{10}$ and a propylene glycol fatty acid ester, wherein the retention rate of reduced coenzyme $Q_{10}$ after being preserved in air at 40° C. for 2 weeks is not less than 80 wt %,
  wherein a fatty acid residue of the propylene glycol fatty acid ester is one or more fatty acid residues selected from the group consisting of caprylic acid, capric acid, lauric acid, myristic acid, palmitic acid, stearic acid, isostearic acid, oleic acid, linoleic acid and linolenic acid, and
  wherein the amount of propylene glycol fatty acid ester in the composition is not less than 20 wt % and the amount of reduced coenzyme $Q_{10}$ in the composition is not more than 40 wt %.

15. The reduced coenzyme $Q_{10}$ of claim 14, wherein the propylene glycol fatty acid ester is acceptable for food or a pharmaceutical product.

16. The reduced coenzyme $Q_{10}$-containing composition of claim 14, wherein the composition further comprises a fat or oil.

17. The reduced coenzyme $Q_{10}$-containing composition according to claim 16, wherein the fat or oil is one or more selected from the group consisting of: coconut oil, palm oil, palm kernel oil, linseed oil, camellia oil, brown rice germ oil, olive oil, rapeseed oil, rice oil, peanut oil, corn oil, wheat germ oil, soybean oil, perilla oil, cottonseed oil, sunflower seed oil, kapok oil, evening primrose oil, shea butter, sal butter, cacao butter, sesame oil, safflower oil, lard, milk fat, fish oil, beef fat, a fat or oil obtained by hydrogenation or transesterification, a medium-chain triglyceride, a partial glyceride of a fatty acid, and phospholipids.

18. The reduced coenzyme $Q_{10}$-containing composition of claim 14, further containing a surfactant other than a propylene glycol fatty acid ester.

19. The reduced coenzyme $Q_{10}$-containing composition of claim 18, wherein the surfactant is one or more selected from the group consisting of a glycerin fatty acid ester, an organic acid monoglyceride, a sucrose fatty acid ester, a condensed ricinoleic acid polyglyceride, a sorbitan fatty acid ester, and a polyoxyethylene sorbitan fatty acid ester.

20. The reduced coenzyme $Q_{10}$-containing composition of claim 16, wherein the fat or oil and/or the surfactant are/is acceptable for food or a pharmaceutical product.

21. The reduced coenzyme $Q_{10}$-containing composition of claim 14, further containing an active ingredient that is not reduced coenzyme $Q_{10}$.

22. The reduced coenzyme $Q_{10}$-containing composition of claim 14, wherein the content of reduced coenzyme $Q_{10}$ in the composition is not less than 1 wt %.

23. The reduced coenzyme $Q_{10}$-containing composition of claim 14, wherein the reduced coenzyme $Q_{10}$ is prepared in the absence of the propylene glycol fatty acid ester and then mixed with the propylene glycol fatty acid ester.

24. The reduced coenzyme $Q_{10}$-containing composition of claim 14, wherein the composition is processed into an oral administration form.

25. The reduced coenzyme $Q_{10}$-containing composition of claim 24, wherein the composition is a capsule.

26. The reduced coenzyme $Q_{10}$-containing composition of claim 25, wherein the capsule is a soft capsule.

27. The reduced coenzyme $Q_{10}$-containing composition of claim 14, wherein the composition is free of an oxidation product of a reducing agent.

28. The reduced coenzyme $Q_{10}$-containing composition of claim 14, wherein the reduced coenzyme $Q_{10}$ is stabilized against oxidation by mixing a propylene glycol fatty acid ester with reduced coenzyme $Q_{10}$ to prepare a composition which protects reduced coenzyme $Q_{10}$ from oxidation, and further comprises providing a surfactant other than a propylene glycol fatty acid ester, wherein the surfactant is one or more selected from the group consisting of a glycerin fatty acid ester, an organic acid monoglyceride, a sucrose fatty acid ester, a condensed ricinoleic acid polyglyceride, a sorbitan fatty acid ester, and a polyoxyethylene sorbitan fatty acid ester.

29. The reduced coenzyme $Q_{10}$-containing composition according to claim 14, wherein the propylene glycol fatty acid ester is one or more selected from the group consisting of propylene glycol monooleate, propylene glycol monocaprylate, propylene glycol dioleate and propylene glycol dicaprylate.

* * * * *